United States Patent [19]

McAleer et al.

[11] 4,296,024

[45] Oct. 20, 1981

[54] HUMAN IMMUNE SERUM GLOBULIN WITH HIGH HEPATITIS A ANTIBODY TITER

[75] Inventors: William J. McAleer, Ambler; William J. Miller, North Wales, both of Pa.

[73] Assignee: Merck & Co., Inc., Rahway, N.J.

[21] Appl. No.: 1,133

[22] Filed: Jan. 5, 1979

Related U.S. Application Data

[63] Continuation-in-part of Ser. No. 813,566, Jul. 7, 1977, abandoned, which is a continuation-in-part of Ser. No. 610,499, Sep. 4, 1975, abandoned, which is a continuation-in-part of Ser. No. 531,020, Dec. 9, 1974, abandoned.

[51] Int. Cl.$^3$ .............................................. C07G 7/00
[52] U.S. Cl. ............................ 260/112 B; 424/85; 424/86; 424/89; 424/101; 424/177
[58] Field of Search ................ 260/112 B; 424/86, 89, 424/101, 85

[56] References Cited

U.S. PATENT DOCUMENTS

| | | | |
|---|---|---|---|
| 3,105,011 | 9/1963 | McLean | 424/89 |
| 4,013,411 | 3/1977 | Shupack et al. | 424/89 |
| 4,017,601 | 4/1977 | Hilleman et al. | 424/89 |
| 4,029,764 | 6/1977 | Provost et al. | 424/89 |

OTHER PUBLICATIONS

Krugman et al., New Eng. J. of Med. 292 (1975), 1141-1143.
Diagnostic Procedures for Viral, Rickettsial & Chlamydial Infections, 5th Ed., Lennette et al., (1979), p. 907.
J. of Infectious Diseases, vol. 134, No. 1, Jul. 1976, Krugman, pp. 70-74.
New England J. of Med., vol. 292, May, 1975, Krugman et al., pp. 1141-1143.
Am. J. Med. Sci., vol. 270, No. 1, 1975, p. 62, Purcell et al.
J. Inf. Dis., vol. 140, No. 4, Oct. 1979, pp. 642-648, Gerety et al.
Southern Med. Journal, vol. 69, No. 4, Apr. 1976, pp. 468-469, Melnick et al.
Holmes, Science, vol. 165, 22 Aug., 1969, pp. 816-817.
Mascoli, PSEBM, vol. 142, (1973), pp. 276-282.
Hansson, Vox Sang., vol. 24, (1973), pp. 95-101.
Gozin, Vox. Sang., vol. 23, (1972), pp. 472-477.
Soulier, Progr. Immunibiol. Std., vol. 5, (1972), pp. 20-24.
Hayakawa, Jap. J. Clin. Med., vol. 28, (1970), pp. 2712-2715.
Provost, P.S.E.B.M., vol. 142, (1973), pp. 1257-1267.
Provost, P.S.E.B.M., vol. 148, (1975), pp. 532-539.
Feinstone, Science, vol. 182, Dec. 1973, pp. 1026-1028.
Bolin, Transfusion, vol. 3, (1963), reprinted in HIM Tests (1969), pp. 21-34.
Melnick, S. Med. J., vol. 69, (1976), pp. 468-469.
Purcell, Amer. J. Med. Sci., vol. 270, Jul. & Aug., 1975, pp. 61-62.

Primary Examiner—Howard E. Schain
Attorney, Agent, or Firm—Donald J. Perrella; Hesna J. Pfeiffer

[57] ABSTRACT

An immune adherence hemagglutination assay for detection of hepatitis A antigen or antibody. Plasma having known high titer of hepatitis A antibody, and gamma globulin having known high titer of hepatitis A antibody.

5 Claims, No Drawings

HUMAN IMMUNE SERUM GLOBULIN WITH HIGH HEPATITIS A ANTIBODY TITER

RELATED APPLICATIONS

This application is a continuation-in-part of copending application Ser. No. 813,566 filed July 7, 1977 which in turn is a continuation-in-part of application Ser. No. 610,499 filed Sept. 4, 1975 which in turn is a continuation-in-part of application Ser. No. 531,020 filed Dec. 9, 1974, all now abandoned.

BACKGROUND OF THE INVENTION

This invention relates to an assay method for hepatitis A antibody and antigen, and to plasma and gamma globulin of known hepatitis A antibody titer. More particularly it relates to an immune adherence assay method and to the use of such method to detect plasma and prepare gamma globulin having a known protective titer of hepatitis A antibody.

Hepatitis A is a liver disease which, while not commonly fatal, can involve many weeks of debilitating illness. It is usually spread by direct contact with an infected individual or by contaminated drinking water or food. Presently known methods for the detection of hepatitis A antigen or antibody lack sensitivity, are time-consuming and expensive. There has not been heretofore a sensitive test which is both specific and reproducible for quickly determining whether or not the sera from a patient or a donor contains hepatitis A associated antibody or antigen. For example, the prior art method for determination of hepatitis A antibody involves neutralization tests in marmoset monkeys. This method takes from 8 to 10 weeks and only permits evaluation of 1 or 2 samples per 100 marmosets.

The present method of treating an individual believed to be in danger of contracting hepatitis A is to administer gamma globulin. The rationale for this treatment is the expectation that the gamma globulin contains hepatitis A antibody in a quantity sufficient to confer immunity to the exposed individual. It is well known, however, that gamma globulin fails to confer immunity to certain exposed individuals.

OBJECTS OF THE INVENTION

An object of the present invention is to provide plasma and gamma globulin having a known, high titer of hepatitis A antibody. A further object is to provide methods for obtaining plasma and gamma globulin containing a high protective titer of hepatitis A antibody. Another object is to provide a method to quickly and accurately determine the presence of hepatitis A antigen or antibody in blood, blood derivatives or clinical samples. These and other objects of the present invention will be apparent from the following description.

SUMMARY OF THE INVENTION

In testing a sample for hepatitis A antigen or antibody, antibody or antigen, respectively, is added to a serial dilution of the sample being tested. Complement is added to the resulting antigen-antibody complex followed by an agent to render the agglutination irreversible. Preselected human type O red blood cells are added and the extent of agglutination is determined.

Human immune serum globulin (gamma globulin) having a known, high titer of hepatitis A antibody is obtained by processing the plasma of groups of preselected donors or by raising an undesirably low titer of hepatitis A antibody in plasma or gamma globulin by addition of gamma globulin of known, high titer. By prescreening donors one can obtain plasma containing about 10,000 IAHA hepatitis A antibody units/ml. Pooling of such high titer plasmas and isolation of the gamma globulin allows the preparation of gamma globulin having greater than about 75,000 IAHA units/ml of hepatitis A antibody. A thus prepared solution can be used to add to low titer gamma globulin solutions to elevate the hepatitis A antibody to at least about 4,000 IAHA units/ml.

DETAILED DESCRIPTION

The following reagents are used in the immune adherence hemagglutination assay (IAHA) of the present invention:

1. GVB. GVB (gelatin-veronal buffer) is veronal buffer containing 1% gelatin.

2. Test sera. Sera or plasmas, of human or animal origin, are used as such with no pretreatment in tests to determine antibody content.

3. Human Immune Serum Globulin. The globulin is diluted 1:10 in GVB to yield a concentration of about 15 mg/ml protein. To one volume of diluted gamma globulin, there is added one volume of 10-50% absorbent material w/v in GVB. Examples of suitable absorbents are kaolin w/v, 25% fullers earth w/v, etc. The stoppered mixture is shaken every 5 minutes for 20 minutes and then centrifuged at 1,500 rpm for 10 minutes and the supernatant recovered for use in the assay. The final globulin dilution is 1:20.

4. Antigen. The hepatitis A (infectious hepatitis) antigen is obtained from the liver of a non-human primate, e.g. a marmoset, infected intravenously with hepatitis A virus according to the method of Mascoli et al., Proc. Soc. Exp. Biol. Med., 142, 276, (1973). The liver is removed at a time when the serum glutamic oxaloacetic transaminase and serum isocitric dehydrogenase enzymes are elevated, which generally occurs at from about 14 to about 40 days after inoculation. The liver is perfused with physiological saline at a pH of from about 6.8 to about 7.8, for example, phosphate buffered saline solution containing 0.005 M sodium phosphate and 0.143 M NaCl, pH 7.2. The liver is then comminuted, ground and added to physiological saline to give a final 10% suspension by weight in the physiological saline. The antigen consists of the supernatant obtained after clarification at low speed centrifugation, e.g., at from about 1,000 to about 2,000 rpm for a short period of time, e.g., for from about 5 minutes to about 15 minutes.

The clarified antigen may then be purified by treatment with kaolin and used directly in the assay or, alternatively, the clarified antigen may be purified by isopycnic banding by density gradient centrifugation techniques. When using cesium chloride the antigen corresponding to a buoyant density of from about 1.32 to about 1.36 g/cm$^3$ is separated for use in the hepatitis A assay. The strength of the antigen is determined by block titration vs. hepatitis A antibody using standard methods.

Optionally, but preferably, the antigen may be inactivated or attenuated in known manner, e.g., by treatment with formaldehyde or other known inactivating substances before being used in the assay of the present invention.

While a specific method has been described herein for obtaining the hepatitis A antigen, it is to be understood that the assay of the present invention is not limited to hepatitis A antigen prepared or obtained in any specific manner.

5. Complement. Freshly bled guinea pig serum is prepared and after removal of cells, is frozen in 0.3 ml aliquots at about −70° C. and stored. The aliquot is removed just before use and diluted with GVB to a level predetermined to give maximum agglutination titer with no interference (as discussed by Mayumi et al., Vox. Sang. 20:178–181 (1971). This dilution is typically from about 1:50 to about 1:100.

6. DTT-EDTA-GVB. A 0.10 M solution of ethylenediaminetetraacetic acid (EDTA) is adjusted to pH 7.5 with 1 N NaOH. To two parts of EDTA, there are added three parts of GVB. To this solution there is added sufficient dithiothreitol (DTT) solid to give a concentration of 3 mg DTT/ml. In lieu of DTT any reducing agent containing a sulfhydryl group such as, e.g., mercaptoethanol, dithioerythritol, and the like, may be used in equivalent amount.

7. Red Blood Cells. Citrated fresh whole blood (human type O) is washed three times in phosphate buffered saline, pH 7.2, suspended to 50% v/v and stored at 5° C. The red blood cells are diluted to from about 0.25% to about 2% in GVB before use. As some lots are not agglutinated in the test, the cells must be tested with known antigen and antibody before actual assay use. The test for screening acceptability of human O type cells is as follows: the red blood cells are washed three times with phosphate buffered saline and tested using a serial dilution of a human immune serum globulin lot of known titer using the proper dilution of the antigen purified, e.g., by isopycnic banding by density gradient centrifugation techniques. The hemagglutination pattern is marked from 0 to 4+ following the technique of Hansson et al., *Vox. Sang.*, 24:95–101 (1973) and Gozin et al., *Vox. Sang.*, 23:472–477 (1972). Acceptable lots give a 4+ agglutination for the known positive human immune serum globulin. Lots giving an agglutination pattern less than 4 are generally less satisfactory.

ANTIBODY ASSAY METHOD

To a suitable U-bottom multiwell assay plate such as those manufactured by Canalco, Cooke, Linbro, etc., 0.05 ml of sample to be tested for antibody is added to well 1 of both row A (control) and row B (assay). To well 1 of row C (antigen control) there is added 0.05 ml of GVB. To wells 2–11 of rows A, B and C, there is added 0.025 ml of GVB using a 0.025 ml pipetting tip. A serial 2-fold dilution is then performed from well 1 to well 11 of rows A, B and C using either manual or automatic tulip diluters. After the dilution is completed, 0.025 ml of GVB is added to all wells of row A, and 0.025 ml of antigen is added to all wells of rows B and C. The plate is covered, mixed for a few minutes, e.g., about 2 minutes on a vibrating shaker to mix the contents of each well, and incubated to permit antigen and antibody to react to form a complex. This incubation takes place at from about 25° C. to about 60° C., preferably at about 37° C. for from about 0.25 hour to about 48 hours, preferably for about 1 hour to about 18 hours.

The multiwell assay plate is then removed from the incubator and 0.025 ml of complement is added to each well. The plate is covered, placed on a vibro mixer for a few minutes, e.g., about 2 minutes, to mix the contents of each well, and then incubated to permit complement to react with the complex. This incubation takes place at from about 25° C. to about 45° C., preferably at about 37° C. for from about 0.25 hour to about 24 hours, preferably for about 40 minutes.

The plate is removed from the incubator and 0.025 ml of DTT-EDTA-GVB is added to each well followed by mixing for a few minutes, e.g., for about 2 minutes on the vibro mixer. Immediately thereafter 0.025 ml of from about 0.25% to about 2%, preferably 1% of human type O red blood cells is added to each well with mixing. After standing at room temperature for at least about 2 hours and up to several days, the wells are read for agglutination. The hemagglutination pattern is marked 0 to 4+. The agglutination is rendered irreversible due to the presence of DTT. The end point for the titration is read as the last well showing a 4+ agglutination.

ANTIGEN ASSAY METHOD

To a suitable U-bottom multiwell assay plate such as those manufactured by Canalco, Cooke, Linbro, etc., 0.025 ml of sample to be tested for antigen is added to well 1 of both row A (control) and row B (assay). To well 1 of row C (antibody control) there is added 0.05 ml of GVB. To wells 2–11 of rows A, B and C, there is added 0.025 ml of GVB using a 0.025 ml pipetting tip. A serial 2-fold dilution is then performed from well 1 to well 11 of rows A, B and C using either manual or automatic tulip diluters. After the dilution is completed, 0.025 ml of GVB is added to all wells of row A, and 0.025 ml of antibody is added to all wells of rows B and C. The plate is covered, mixed for a few minutes, e.g., about 2 minutes on a vibrating shaker to mix the contents of each well, covered and incubated to permit antigen and antibody to react to form a complex. This incubation takes place at from about 25° C. to about 60° C., preferably at about 37° C., for from about 0.25 hour to about 48 hours, preferably for about 1 hour to about 18 hours.

The multiwell assay plate is then removed from the incubator and 0.025 ml of complement is added to each well. The plate is covered, placed on a vibro mixer for a few minutes, e.g., about 2 minutes to mix the contents of each well, and then incubated to permit complement to react with the complex. This incubation takes place at from about 25° C. to about 45° C., preferably at about 37° C., for from about 0.25 hour to about 24 hours, preferably for about 40 minutes.

The plate is removed from the incubator and 0.025 ml of DTT-EDTA-GVB is added to each well followed by mixing for a few minutes, e.g., for about 2 minutes on the vibro mixer. Immediately thereafter 0.025 ml of from about 0.25% to about 2%, preferably 1% of human type O red blood cells is added to each well with mixing. After standing at room temperature for at least about 2 hours and up to several days, the wells are read for agglutination. The hemagglutination pattern is marked 0 to 4+. The agglutination is rendered irreversible due to the presence of DTT. The end point for the titration is read as the last well showing a 4+ agglutination.

The antigen used in the assay of the present invention is described in greater detail in a copending application of Philip J. Provost, Oswald L. Ittensohn and Maurice R. Hilleman, entitled "Hepatitis A Antigen" filed Dec. 9, 1974, now U.S. Pat. No. 4,029,764. The disclosure of that patent is hereby incorporated by reference.

The immunoassay method of the present invention has wide applicability in the detection and treatment of hepatitis A. The assay can be used to determine the presence of hepatitis A antigen or antibody in humans or animals. It can be used by hospitals, by physicians and by medical laboratories. It can be used to determine to amount of hepatitis A antibody in human immune serum globulin which is derived from plasma which in turn is obtained from donors of whole blood.

It has been found that the protective level of hepatitis A antibody in gamma globulin is at least about 4,000 IAHA units/ml. It has further been found by means of the antibody assay of the present invention that some lots of gamma globulin have either no hepatitis A antibody or a level so low as to be ineffective to confer immunity. This explains the known inability of gamma globulin to protect exposed individuals in some cases: if the gamma globulin contains no hepatitis A antibody or an undesirably low level, i.e., below about 4,000 IAHA units/ml, the exposed individual, unless already possessing indigenous hepatitis A antibody, is likely not to be protected against the disease.

It has been found that gamma globulin prepared from different groups of blood donors differ significantly in levels of hepatitis A antibody. Gamma globulin derived from plasma obtained from donors from the general population (about ⅔ of all plasma) has a hepatitis A antibody content below about 100 IAHA units/ml. On the other hand, gamma globulin derived from plasma obtained from commercial blood banks contains a level of hepatitis A antibody of only from about 200 to about 600 IAHA units/ml. Thus, gamma globulin having a protective level against hepatitis A antibody, i.e., about 4,000 IAHA units/ml or above, is most likely to be obtained by processing plasma obtained from commercial blood banks separately from plasma obtained from general population donors. The resulting gamma globulin generally has a hepatitis A antibody titer of at least about 4,000 IAHA units/ml or higher, and can be used as such or combined in calculated amount with a predetermined amount of gamma globulin obtained from plasma of general population donors having a hepatitis A antibody titer below about 4,000 IAHA units/ml to yield a product having a hepatitis A antibody titer of at least about 4,000 IAHA units/ml.

By employing the IAHA assay of the present invention, individual plasma donors are able to be identified and located whose plasma contains 5,000 to 20,000 IAHA units/ml of hepatitis A antibody. These donors are found to occur in about 0.5% of the population. By combining the plasmas from these donors one is able to prepare for the first time a gamma globulin preparation which contains from about 75,000 to about 300,000 IAHA hepatitis A antibody units/ml. The inherent value of this type of high titer gamma globulin is in its use in adding to subpotent (<4,000 IAHA units/ml) gamma globulin powders or liquids to raise the hepatitis A antibody titer ≧4,000 IAHA units/ml.

The following examples illustrate the present invention without, however, limiting the same thereto.

EXAMPLE 1

Samples of human immune serum globulin from 26 commercial lots are prepared for assay as described previously for the Human Immune Serum Globulin (Reagent 3) using 25% kaolin as absorbent. The samples are then titered for the hepatitis A antibody according to the foregoing method and the following results are obtained:

| Hepatitis A Immunoassay Titer | Lots |
| --- | --- |
| 1:100 | 5 |
| 1:200 | 0 |
| 1:400 | 0 |
| 1:800 | 1 |
| 1:1,600 | 4 |
| 1:3,200 | 11 |
| 1:6,400 | 4 |
| 1:12,800 | 0 |
| 1:25,600 | 1 |

A positive antibody response (titer ≧1:800) is found in 21 of the 26 lots. Five of the lots, however, have titers ≦1:100 and are essentially devoid of antibody. These five lots would be ineffective in protecting a subject exposed to the hepatitis A virus.

EXAMPLE 2

The hepatitis A antibody titers are assayed for a group of 3 individuals diagnosed as having hepatitis B by demonstrating HB$_s$Ag (Australia antigen) in the sera, and compared with sera from the same individuals taken before onset of the hepatitis B:

| Individual | Day Specimen Taken (Clinical onset of hepatitis B is taken as day zero) | | Hepatitis A Immunoassay Titer |
| --- | --- | --- | --- |
| 1 | − | 108 | 5 |
|   | + | 10 | 5 |
|   | + | 149 | 5 |
| 2 | − | 27 | 2,560 |
|   | − | 7 | 5,120 |
|   | + | 192 | 2,560 |
| 3 | − | 4 | 640 |
|   | + | 8 | 640 |
|   | + | 190 | 640 |

None of the 3 individuals shows a significant change in hepatitis A antibody development during the course of his illness indicating lack of hepatitis A antibody development and demonstrating that the assay is specific for hepatitis A antibody. These test results are in agreement with complement fixation test results.

EXAMPLE 3

A sample of antigen prepared as described previously for Antigen (Reagent 4) is assayed according to the antigen assay method described herein against known antibody and the following data are obtained:

| Well | Dilution | Agglutination |
| --- | --- | --- |
| 1 | 1:1 | 4+ |
| 2 | 1:2 | 4+ |
| 3 | 1:4 | 4+ |
| 4 | 1:8 | 4+ |
| 5 | 1:16 | 4+ |
| 6 | 1:32 | 2+ |

EXAMPLE 4

300 Liters of plasma collected randomly as individual 400 ml units from commercial blood donor centers are pooled and processed to gamma globulin according to the conventional Cohn alcohol precipitation method. The resulting powder, 13.8 kg, is taken up in 63 liters of sterile, pyrogen-free saline solution. When tested according to the immunological assay of the present invention, the lot is found to have an average titer of 5,000 IAHA units/ml.

EXAMPLE 5

The individual plasmaphoresis units from commercial blood donor centers are assayed via the immunological assay of the present invention. From 59 units (approximately 400 ml each) 7 are found that have titers of 1:2,560 or higher. The subsequent units from these donors are collected separately until approximately 100 liters are on hand. This pool is processed by the Cohn alcohol precipitation method to yield 0.5 kg of powder. The powder is taken up in 2.1 liters of sterile pyrogen-free saline solution. When assayed by the immunological assay of the present invention, the lot is shown to have an average hepatitis A antibody titer of 25,000 units/ml.

EXAMPLE 6

Plasma, 1,000 liters, obtained from general population donors is pooled and treated according to the conventional Cohn alcohol precipitation method to yield 25,000 ml of gamma globulin. The gamma globulin is tested according to the immunological assay of the present invention and found to have a hepatitis A antibody titer of 1,000 IAHA units/ml. This low titer of hepatitis A antibody would leave an exposed individual at risk.

EXAMPLE 7

A lot of gamma globulin derived from plasma obtained from a commercial blood bank is tested according to the immunological assay of the present invention and found to have a hepatitis A antibody titer of 4,000 IAHA units/ml. A second lot of gamma globulin derived from plasma obtained from prisoners at a state prison is tested according to the immunological assay of the present invention and found to have a hepatitis A antibody titer of 6,400 IAHA units/ml. Each of these lots has an acceptable titer of hepatitis A antibody.

EXAMPLE 8

In order to utilize the 30,000 ml of gamma globulin prepared in Example 6, it is necessary to increase its hepatitis A antibody titer to 4,000 IAHA units/ml. As a commercial lot contains 63,000 ml, this is done by adding 5,500 ml of the 4,000 titer material and 27,500 ml of the 6,400 titer material from Example 7. These amounts are determined in the following manner. Thus, if X, Y and Z represent the volumes, respectively, of the gamma globulin of Examples 6 and 7, the total volume of $X+Y+Z$ is 63,000 ml, or: (1) $30,000+Y+Z=63,000$ ml. Since each ml will contain 4,000 IAHA units of hepatitis A antibody: (2) $30,000 (1,800)+Y (4,000)+Z (6,400)=252,000,000$. By multiplying eq. 1 by 4,000 and subtracting the resulting equation 1a from eq. 2:

```
(2)    54,000,000 + Y (4,000) + Z (6,400) = 252,000,000
(1a) −120,000,000 − Y (4,000) − Z (4,000) = 252,000,000
     −66,000,000              + Z (2,400) = 0
                                   2,400Z = 66,000,000
                                        Z =    27,500 ml
```

The volume of Y, by difference, is 5,500 ml.

EXAMPLE 9

Samples of human immune serum globulin from 6 commercial manufacturers are prepared for assay as described previously for the Human Immune Serum Globulin (Reagent 3) using 25% kaolin as absorbent. The samples are then titered for the hepatitis A antibody according to the foregoing method and the following results are obtained:

| Gamma Globulin Manufacturers | Hepatitis A IAHA Antibody Titer |
|---|---|
| A | <100 |
| B | 320 |
| C | 1,000 |
| D | 2,000 |
| E | 4,000 |
| F | 8,000 |

A range in hepatitis A antibody titer of from <1:100 to 1:8,000 is found. The lots made by manufacturers A, B, C and D would be unlikely to render protection against hepatitis A.

EXAMPLE 10

Plasma having a hepatitis A antibody titer of <8,000 IAHA units/ml is obtained from donors selected using the IAHA assay of the present invention. 1.3 Liters of this plasma are processed through the Cohn ethanol fractionation process to yield a lyophilized gamma globulin powder weighing 8.1 g. One gram of this powder is made up into a 16.5% w/v solution. This solution has 80,000 IAHA units/ml of hepatitis A antibody. A 1 g sample from a 2 kg lot of gamma globulin prepared from plasma from unselected donors is made up into a 16.5% w/v solution and is found to have 2,000 IAHA units/ml of hepatitis A antibody. To each ml of a solution of potency 2,000 IAHA units/ml there is added 0.025 ml of the 80,000 IAHA units/ml lot. The resulting mixture is stirred for 15 minutes. Reassay of the blended gamma globulin powders shows a titer of 4,000 IAHA units/ml of hepatitis A antibody.

EXAMPLE 11

The individual plasmaphoresis units from commercial blood donor centers are assayed via the immunological assay of the present invention. From 1,200 units (approximately 400 ml each) 7 are found that have titers of 1:10,000 or higher. The subsequent units from these donors are collected separately until approximately 100 liters is on hand. This pool is processed by the Cohn alcohol precipitation method to yield 0.5 kg of powder. The powder is taken up in 2.1 liters of sterile pyrogen-free saline solution. When assayed by the immunological assay of the present invention, the lot is shown to have an average titer of 120,000 units/ml.

EXAMPLE 12

100 Liters of plasma collected randomly as individual 400 ml units from commercial blood donor centers are pooled and processed to gamma globulin according to the conventional Cohn alcohol precipitation method. The resulting powder, 0.46 kg, is taken up in 2.5 liters of sterile, pyrogen-free saline solution. When tested according to the immunological assay of the present invention, the lot is found to have an average titer of 4,000 IAHA units/ml.

EXAMPLE 13

A 16.5% gamma globulin solution to be assayed for hepatitis A antibody content by the immune adherence hemagglutination assay is first diluted 1-10 in gelatin buffer (as previously described) and to it is added an equal volume of 25% w/v Kaolin suspension. The mixture is stoppered and shaken every 5 minutes for 20 minutes and then centrifuged at 1,500 rpm for 10 minutes and the supernatant recovered for use in the assay.

To a suitable U-bottom multiwell assay plate such as those manufactured by Canalco, Cooke, Linbro, etc., 0.05 ml of sample to be tested for antibody is added to well 1 of both row A (control) and row B (assay). To well 1 of row C (antigen control) there is added 0.05 ml of GVB. To wells 2-11 of rows A, B and C, there is added 0.025 ml of GVB using a 0.025 ml pipetting tip. A serial 2-fold dilution is then performed from well 1 to well 11 of rows A, B and C using either manual or automatic tulip diluters. After the dilution is completed, 0.025 ml of GVB is added to all wells of row A, and 0.025 ml of antigen is added to all wells of rows B and C. The plate is covered, mixed for a few minutes, e.g., about 2 minutes on a vibrating shaker to mix the contents of each well, and incubated to permit antigen and antibody to react to form a complex. This incubation takes place at from about 25° C. to about 60° C., preferably at about 37° C. for from about 0.25 hour to about 48 hours, preferably for about 1 hour to about 18 hours.

The multiwell assay plate is then removed from the incubator and 0.025 ml of complement is added to each well. The microtiter plate is covered, placed on a vibro mixer for a few minutes, e.g. about 2 minutes to mix the contents of each well, and then incubated to permit complement to react with the complex. This incubation takes place at from about 25° C. to about 45° C., preferably at about 37° C. for from about 0.25 hour to about 24 hours, preferably for about 40 minutes.

The plate is removed from the incubator and 0.025 ml of DTT-EDTA-GVB is added to each well followed by mixing for a few minutes, e.g. for about 2 minutes, on the vibro mixer. Immediately thereafter 0.025 ml of from about 0.25 to about 2%, preferably 1% of human type O red blood cells is added to each well with mixing. After standing at room temperature for at least about 2 hours, the wells are read for agglutination. The titer of this gamma globulin solution is found to be 1:2,000.

What is claimed is:

1. Human immune serum globulin having a hepatitis A antibody titer of at least about 75,000 IAHA units/ml.

2. A method of preparing human immune serum globulin having a hepatitis A antibody titer of at least about 75,000 IAHA units/ml which comprises selecting a donor having a hepatitis A antibody titer above about 5,000 IAHA units/ml, obtaining plasma from the donor, and preparing gamma globulin therefrom.

3. Human immune serum globulin prepared according to the method of claim 2.

4. A method of preparing human immune serum globulin having a hepatitis A antibody titer of at least about 4,000 IAHA units/ml which comprises adding a predetermined amount of human immune serum globulin having a hepatitis A antibody titer above about 75,000 IAHA units/ml to a predetermined amount of human immune serum globulin having a hepatitis A antibody titer below about 4,000 IAHA units/ml.

5. Human immune serum globulin prepared according to the method of claim 4.

* * * * *